United States Patent [19]
Psaros

[11] Patent Number: 6,095,139
[45] Date of Patent: Aug. 1, 2000

[54] VENTILATOR SUITABLE FOR MINIATURIZATION

[75] Inventor: Georgios Psaros, Tullinge, Sweden

[73] Assignee: Siemens Elema AB, Solna, Sweden

[21] Appl. No.: 09/149,023

[22] Filed: Sep. 8, 1998

[30] Foreign Application Priority Data

Sep. 11, 1997 [SE] Sweden ................................. 9703290

[51] Int. Cl.[7] ................................................ A61M 16/00
[52] U.S. Cl. ................................ 128/204.22; 128/204.21
[58] Field of Search ........................ 128/204.18, 204.22, 128/204.23, 204.25, 204.21

[56] References Cited

U.S. PATENT DOCUMENTS

| | | | |
|---|---|---|---|
| 4,163,450 | 8/1979 | Kirk et al. .......................... | 128/204.23 |
| 4,681,099 | 7/1987 | Sato et al. .......................... | 128/204.23 |
| 5,423,313 | 6/1995 | Olsson et al. ....................... | 128/204.22 |
| 5,495,848 | 3/1996 | Aylsworth et al. .................. | 128/207.18 |
| 5,664,563 | 9/1997 | Schroeder et al. .................. | 128/204.24 |
| 5,832,917 | 11/1998 | Sarela et al. ...................... | 128/204.22 |
| 5,850,835 | 12/1998 | Takaki et al. ...................... | 128/204.18 |
| 5,873,361 | 2/1999 | Hakala ............................... | 128/204.22 |
| 5,915,381 | 6/1999 | Nord .................................. | 128/204.18 |
| 5,918,596 | 7/1999 | Heinonen ........................... | 128/204.22 |
| 5,931,163 | 8/1999 | Stegmann et al. .................. | 128/204.18 |

FOREIGN PATENT DOCUMENTS

| | | |
|---|---|---|
| 0 691 134 | 1/1996 | European Pat. Off. . |
| 2 724 322 | 3/1996 | France . |
| WO 94/06499 | 3/1994 | WIPO . |

*Primary Examiner*—John G. Weiss
*Attorney, Agent, or Firm*—Hill & Simpson

[57] ABSTRACT

A ventilator includes a gas flow generator for generating a gas with an adjustable pressure and/or flow rate, an inspiratory line with a proximal end, connected to the gas flow generator and a distal end, devised for connection to a patient, an expiratory valve connected to the inspiratory line at a specific distance from the distal end of the inspiratory line to evacuate gas exhaled by the patient, a pressure gauge and/or a flow meter arranged to measure pressure and/or the rate of gas flow in the inspiratory line and a control unit for controlling at least the maintenance of a positive end-expiratory pressure (PEEP). For PEEP to be maintained in a simple and reliable manner, the ventilator is devised with the pressure gauge and/or the flow meter connected to the inspiratory line between the expiratory valve and the distal end of the inspiratory line, and the control unit is devised to open the expiratory valve and regulate, on the basis of the pressure and/or flow measured, a flow of gas through the inspiratory line during expiration so that the desired positive end-expiratory pressure is maintained.

10 Claims, 2 Drawing Sheets

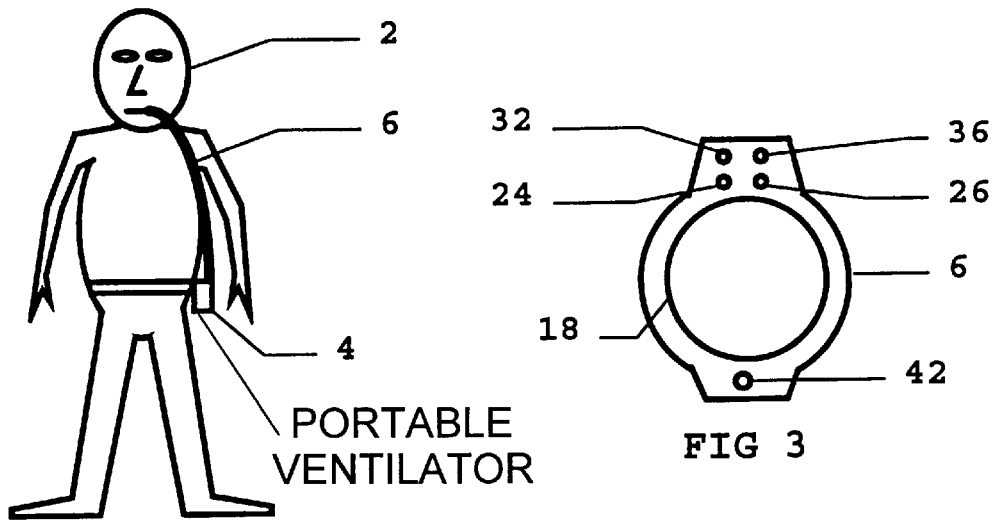
FIG. 1
FIG 3
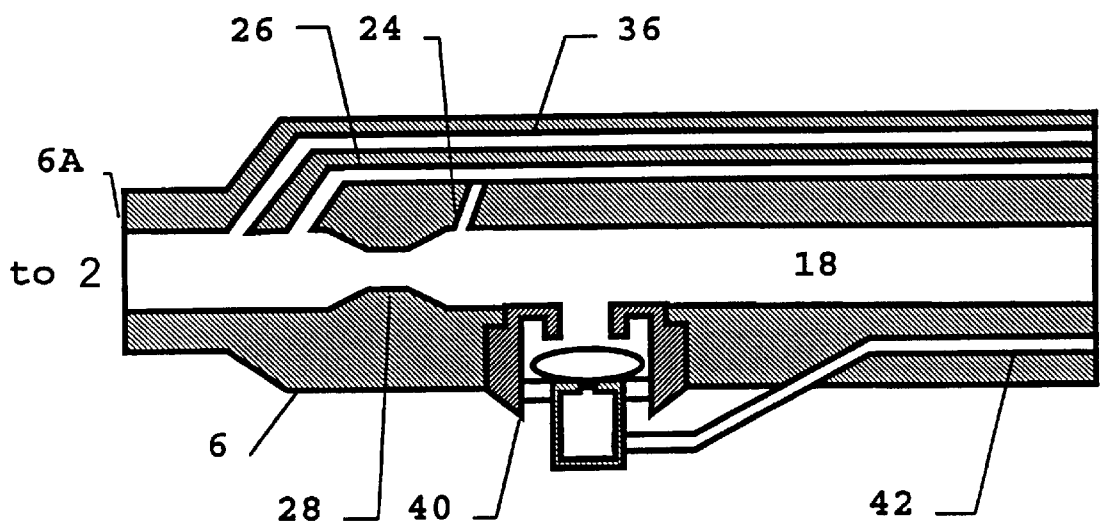
FIG 4

VENTILATOR SUITABLE FOR MINIATURIZATION

BACKGROUND OF THE INVENTION

1. Field of the Invention

The present invention is directed to a ventilator of the type having a gas flow generator for generating a flow of gas at pre-adjustable pressure and/or flow rate, an inspiratory line with a proximal end connected to the gas flow generator and a distal end adapted for connection to a patient, an expiratory valve connected to the inspiratory line at a specific distance from the distal end of the inspiratory line to evacuate gas exhaled by the patient, a pressure gauge and/or a flow meter disposed to measure the pressure and/or flow rate of gas in the inspiratory line, and a control unit for controlling at least the maintenance of a positive end-expiratory pressure (PEEP).

2. Description of the Prior Art

A ventilator of the above type is described in PCT Application WO 94/06499. This known ventilator has an inspiratory line connected to a gas source at one end and to the patient at the other end. An expiratory valve is connected to the inspiratory line at a specific distance from the patient. In one embodiment, the expiratory valve is connected to a second gas source for the purpose of maintaining a pre-adjustable Positive End-Expiratory Pressure (PEEP). In another embodiment, the expiratory valve is instead connected to the gas source via a valve system in order to maintain PEEP. A pressure gauge and flow meter are arranged in the inspiratory line between the gas source and the expiratory valve. A control unit controls the entice ventilator. This known ventilator is primarily intended for use as a home care ventilator, i.e. a respirator a patient can use at home.

Another known ventilator is described in French Patent 2 724 322. This known ventilator has an inspiratory line connected to a gas source at one end and to the patient at the other end. An expiratory valve is connected to the inspiratory line at a specific distance from the patient. The expiratory valve can be regulated to maintain a pre-selected PEEP. A pressure gauge is arranged in the inspiratory line between the gas source and the expiratory valve. A volume meter can be arranged between the gas source and the expiratory valve, downstream of the expiratory valve or between the expiratory valve and the patient, for measuring inhaled and exhaled volumes, respectively. During expiration there is no flow from the gas source through the inspiratory line. This known ventilator also could be used as a home care ventilator.

Interest in home care ventilators is steadily increasing. This is because such a device is advantageous to the patient, who is able to be in her/his own home and can enjoy a greater degree of mobility. There are also public health benefits, since home care frees hospital resources by reducing in-patient treatment time, beds in intensive care being particularly costly. This type of ventilator can be battery-powered and is sometimes referred to as a 'portable' ventilator. Despite this terminology, such a ventilator usually weighs quite a few kilograms and can only be carried around with some difficulty, even by healthy people.

A genuinely portable ventilator, i.e. a ventilator (weighing up to 1 kg, preferably less than 500 g) the patient is easily able to carry, with a capacity sufficient to provide respiratory assistance for several hours, would be even more desirable for patients. Miniaturizing a ventilator to this extent, employing modern turbine, battery and microprocessor technology etc., is thoroughly feasible. One important factor in this process would be to retain every essential function available in a conventional ventilator, such as the ability to maintain a PEEP, to as large an extent as possible. Such a fully portable ventilator would be suitable for virtually every kind of patient. It even could be used as an emergency ventilator for a number of applications and could be included in the basic equipment of e.g. aircraft, buses, boats, ambulances, fire engines, etc.

The relative complexity of the way in which PEEP is maintained is a shortcoming of the first described known ventilator described above, since it utilizes a second source of gas or a valve system formed by a number of valves.

SUMMARY OF THE INVENTION

An object of the present invention is to provide a ventilator capable of maintaining PEEP in a simple and reliable manner.

Another object of the present invention is to provide a ventilator which is primarily suitable for miniaturization into a fully portable ventilator.

The above object is achieved in accordance with the principles of the present invention in a ventilator of the type initially described wherein the pressure gauge and/or the flow meter is/are connected to the inspiratory line between the expiratory valve and the distal end of the inspiratory line, and wherein the control unit causes the expiratory valve to open and the control unit regulates the flow of gas through the inspiratory line during expiration, on the basis of the measured pressure and/or the measured flow rate, so that the positive end-expiratory pressure is maintained.

When the pressure gauge and/or flow meter is arranged between the expiratory valve and the distal end of the inspiratory line, the pressure and/or flow of gas from the patient can be measured during exhalation. The control unit can use the measurement signals for calculating and regulating a flow of gas from a gas flow generator, this flow of gas flowing through the inspiratory line to the expiratory valve, and maintaining a PEEP for the patient.

Placing pressure/flow rate measurement functions near the patient also means that every attempt by the patient to inhale can be sensed in a simple and reliable manner. The patient can then be provided with rapid assistance for a new inspiration (inhalation). A flow of breathing gas is also already present at the expiratory valve. When this valve is closed, an inspiratory gas flow at a specific pressure and with a specific flow rate profile can be rapidly generated and supplied to the patient. This rapid response to attempted inspiration is not available with the aforementioned known ventilators.

Thus, the ventilator can be devised so channels for the pressure gauge and/or flow meter are arranged in the wall of the inspiratory line, generally parallel to the gas flow channel carrying breathing gas. The channels open into the gas flow channel between the expiratory valve and the distal end. The other ends of the channels terminate suitably at the proximal end of the inspiratory line. The gauge/meter can then be located in the same enclosure that holds the gas flow generator. This saves space and simplifies connection of the inspiratory line.

Additional channels from which gas samples can be extracted or for introducing additive gases, such as NO and $O_2$, or medication can be arranged in the corresponding manner in the wall of the inspiratory line. These channels can also appropriately open into the gas flow channel between the expiratory valve and the distal end.

When the inspiratory line is devised with a constriction between the expiratory valve and the distal end, a pressure drop develops which is related to the flow rate. Measuring pressure on either side of the constriction may then be sufficient for obtaining values for both pressure and the rate of flow.

The expiratory valve is appropriately an ON/OFF valve. It can be pneumatically controlled, by means of a valve-closing gas pressure supplied by the gas flow generator. The expiratory valve can be pneumatically connected to the gas flow generator via a separate channel arranged in the wall of the inspiratory line.

The gas flow generator can be devised in a number of different ways and can contain different sub-components. In a particularly advantageous embodiment, however, the gas flow generator can be formed by a turbine, a pressure tank and a control valve, all inter-connected in series. The gas flow generator can be miniaturized in an advantageous fashion.

DESCRIPTION OF THE DRAWINGS

FIG. 1 shows the use of a fully portable ventilator according to the invention.

FIG. 3 shows a cross-section of the inspiratory line of FIG. 2

FIG. 4 shows part of the ventilator according to the invention.

DESCRIPTION OF THE PREFERRED EMBODIMENTS

Figure 2:
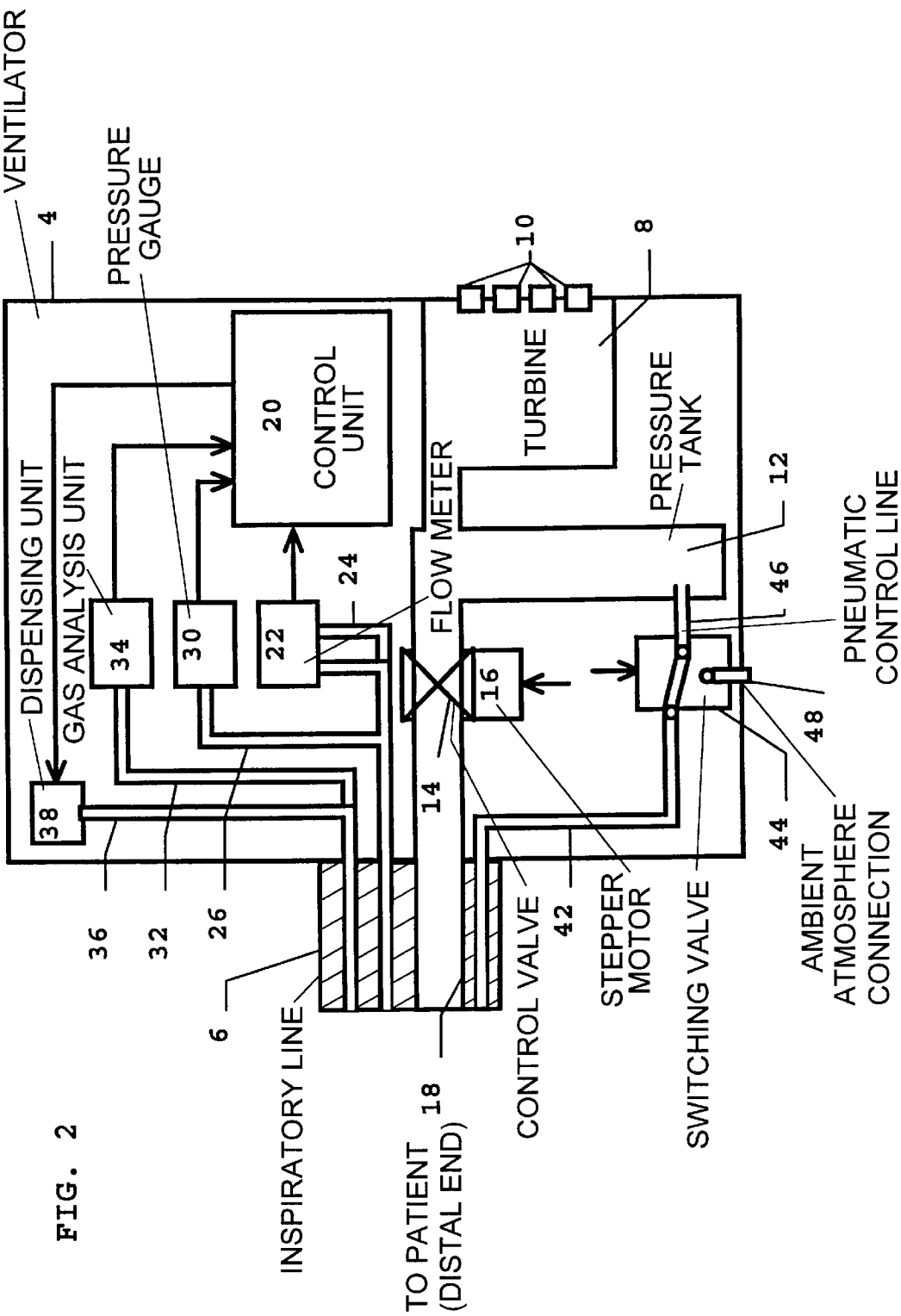
FIG. 2 shows part of an inspiratory line in the ventilator according to the invention.

FIG. 1 shows how a patient 2 can become almost completely mobile with the aid of a fully portable ventilator 4. The patient 2 is connected to the ventilator 4 in some suitable fashion via an inspiratory line 6. Connecting the fully portable ventilator 4 via a nasal route is preferable, since the patient 2 would then find it easier to speak and communicate with others. It should be noted that the fully portable ventilator 4 can also be connected in other ways, e.g. via a face mask, tracheal tube or tracheostomy/ tracheotomy tube. The latter implements are preferable when the ventilator 4 is used in emergencies or for patients 2 requiring greater breathing assistance.

One embodiment of the ventilator 4, including the inspiratory line 6, will now be described, referring simultaneously to FIGS. 2, 3, 4 showing different parts of a ventilator system. Gas flow and pressure are generated by a turbine 8 connected to the atmosphere in some suitable fashion, e.g. via a number of openings 10 or the like. These openings 10 can also be equipped with filters to prevent any particles from being carried down into the lungs. The turbine 8 is connected to a pressure tank 12 holding breathing gas at a specific pressure generated by the turbine 8. The purpose of the pressure tank 12 is to make delivery to the patient 2 of breathing gas at a desired pressure and flow rate faster than if the turbine 8 were to generate pressure and flow from zero. The pressure tank 12 is relatively small, so it occupies less space and shortens the rise time for a pressure increase with a smaller volume. A control valve 14 is arranged after the pressure tank. In this instance, the control valve 14 is a 'scissors' valve regulated by a stepper motor 16. The control valve 14 regulates the flow of gas from the pressure tank 12 into a gas flow channel 18 in the inspiratory line 6. The control valve 14 is also small, thereby enabling it to respond more rapidly to control signals (small inertia). This results, in turn, in the delivery of breathing gas, via the control valve 14, with steep gas pressure gradient. The gas flow channel 18 carries breathing gas to the patient 2 at the distal end 6A of the inspiratory line 6.

The turbine 8, pressure tank 12, control valve 14 and stepper motor 16 jointly constitute a gas flow generator capable of generating an optional gas flow in the flow rate and pressure ranges relevant in the treatment of different kinds of patients. Although this construction of the gas flow generator is advantageous, especially in achieving full portability of the ventilator 4, the gas flow generator can have other components. For example, a compressor or fan can replace the turbine 8. The turbine 8 can also be replaced with a pressurized source of gas, such as a gas cylinder or a piped compressed air system. The pressure tank 12 can be resilient or non-resilient or can be dispensed with completely. A resilient pressure tank can contribute to the generation of higher pressures by being compressible. In principle, the control valve 14 can be any kind of known valve. The stepper motor 16 can be dispensed with or replaced by some other known actuator, depending on the choice of the control valve 14. The components of the gas flow generator affect the size and portability of the ventilator 4. In principle, however, the same functionality can be achieved regardless of the components employed. The exact components used in the gas flow generator are not crucial to application of the invention.

The turbine 8 and the stepper motor 16 are controlled by a control unit 20. The control unit 20 can be formed by hardware, or by software or a combination thereof. The control unit 20 controls all functions in the ventilator 4 so parameter settings (made via a user interface, not shown) are maintained. The control unit 20 receives information on pressure and flow for use in maintaining those functions. Flow information is received from a flow meter 22 which is connected to the distal end of the inspiratory line 6 via a first channel 24 and a second channel 26. In principle, the channels 24, 26 proceed parallel to the gas flow channel 18 in the wall of the inspiratory line 6 and open onto either side of a constriction 28 in the gas flow channel 18. The pressure of the gas drops when it flows through the constriction 28, the magnitude of the drop being related to the magnitude of the flow. Flow through the flow meter 22 therefore can be determined by measuring pressure on either side of the constriction 28. Since pressure is employed in this instance for determining the flow rate, the second channel 26 can be connected to a pressure gauge 30 in order to measure pressure at the distal end 6A of the inspiratory line 6.

It should be noted that other flow meters, suitable for placement near the distal end 6A, can replace the flow meter 22. A separate channel would then be necessary for the pressure gauge 30. Since the flow meter 22 determines the flow rate from the pressure drop across the constriction 28, the pressure signal can be obtained straight from the flow meter 22 instead of from a separate pressure gauge 30.

A gas sampling channel 32, which terminates at the distal end 6A, extends through the inspiratory line 6. Gas samples can be taken from the gas sampling channel 32 and analyzed in a gas analysis unit 34. The gas analysis unit 34 appropriately contains a pump for extracting the gas samples to be analyzed. Gas analysis can be performed to monitor carbon dioxide levels or check to ensure that sufficient breathing assistance is being provided. Gas analysis can also be performed to check on the composition of the breathing gas being supplied to the patient 2. If the gas and flow meters used are fast enough, carbon dioxide output and oxygen consumption can also be determined.

The latter is of interest when the inspiratory line 6 contains a dispensing channel 36 for dispensing an additive gas to the patient 2. The dispensing channel 36 is connected to a dispensing unit 38 and opens into the gas flow channel 18 at the distal end 6A. The dispensing unit 38 includes a small gas cylinder containing additive gas and has a dispensing valve for regulating the amount dispensed. The additive gas can be oxygen or some other gas, such as NO. The dispensing unit 38 can also hold medication or some liquid additive which is dispensed through the dispensing channel 36 into the gas flow channel 18. The additive can be vaporized in this channel or dispersed in small droplets before being delivered to the patient 2.

An expiratory valve 40 is also connected to the inspiratory line 6. In the illustrated example, the expiratory valve 40 is built into the wall of the inspiratory line 6 so it occupies as little space as possible. A tube or the like can also be connected between the inspiratory line 6 and the expiratory valve 40 without affecting its function (as described below).

The expiratory valve 40 is connected to the gas flow channel 18 so that the constriction 28 and the openings of the channels 24, 26, 32, 36 lie between the expiratory valve 40 and the distal end 6A.

In this embodiment, the expiratory valve 40 is a pneumatically controlled ON/OFF valve (e. g. a mushroom valve). It is connected to the pressure tank 12 via a control channel 42 and a switching valve 44. The control channel 42 proceeds in the wall of the inspiratory line 6, parallel to the gas flow channel 18 and other channels 24, 26, 32, 36. The switching valve 44 is controlled by the control unit 20.

During inspiratory phases (inhalation phases), the switching valve 44 is in a first position in which the control channel 42 is connected to the pressure tank 12 via a first gas connection 46. The expiratory valve 40 is then closed with the same actuating pressure (usually higher than the pressure of the breathing gas delivered to the patient 2) as the pressure in the pressure tank 12.

During expiratory phases, the switching valve 44 is switched to a second position in which the expiratory valve 40 is connected to the atmosphere via the control channel 42, the switching valve 44 and a second gas connection 48.

If a positive end-expiratory pressure (PEEP) is to be maintained for the patient 2, the control valve 14 is regulated so that a flow of gas is released through the gas flow channel 18 toward the patient 2, even during expiration. This flow of gas is controlled by the control unit 20 according to the pressure and flow measured between the expiratory valve 40 and the distal end 6A. This regulated flow of gas also flows out through the expiratory valve 40 but simultaneously serves as resistance in relation to the patient 4, who accordingly exhales against a pressure corresponding to the selected PEEP.

This kind of PEEP regulation was not previously possible, S especially not in portable ventilators. Here, the placement of pressure/flow measurement between the expiratory valve 40 and the distal end 6A (the patient 2) plays a decisive role. PEEP cannot be regulated and maintained in this way unless information is available on pressure/flow at the patient 2.

This location for pressure/flow measurement also produces other advantages. For example, the ventilator 4 can be made to respond more rapidly to any efforts by the patient 2 to inhale (i.e. triggering). The ventilator 2 can in particular respond immediately to any inspiration commenced during expiration. Flow will then be registered as moving towards the patient 2, and the control unit 20 can respond immediately, closing the expiratory valve 40 and introducing an inspiratory flow of gas. This flow commences relatively quickly, since a flow of gas is already being maintained through the gas flow channel 18.

The placement of just about all the components in a common enclosure, with all the necessary gas channels arranged in the inspiratory line 6, makes the ventilator 4 very compact and easy to use. The few parts (the enclosure and inspiratory tube 6) are interconnected in a suitable fashion. For example, known types of bayonet or pin (keyed) index connectors can be used. No additional cords or tubing, which could become entangled with each other or other objects, are needed.

As noted above, the described embodiment is one advantageous version of a fully portable ventilator, but the embodiment can be utilized for a number of different applications. For example, it can be used as a home care ventilator for patients who do not require constant monitoring. It can also be used in ambulances or as an emergency ventilator. A third option is to use it for non-acute (non-critical care) treatment in hospitals. In other words, it can be employed for virtually every application for which a ventilator is needed.

The portable ventilator is battery-powered. The batteries can naturally be rechargeable, and the provision of a parallel AC power source is a an option.

The ventilator does not need to incorporate every option. The ventilator 4 can be devised in both simpler and more complex versions. In principle, a simple version includes the turbine 8, pressure tank 12, control valve 14, stepper motor 16, control unit 20, flow meter 22 (doubling as a pressure gauge), inspiratory line 6 (with the channels 18, 24, 26 and 42), expiratory valve 40, switching valve 44 and batteries (not shown). This kind of simple version of the ventilator 4, utilizing existing components, can be manufactured in about the same size as a portable cassette or CD player, i.e. about 10×10×2 cm and weigh a few hundred grams.

Although modifications and changes may be suggested by those skilled in the art, it is the intention of the inventor to embody within the patent warranted hereon all changes and modifications as reasonably and properly come within the scope of his contribution to the art.

I claim as my invention:

1. A ventilator comprising:

a gas flow generator which generates a flow of gas with at least one pre-selectable parameter value selected from the group of parameter values comprising pressure and flow rate;

an inspiratory line having a proximal end connected to said gas flow generator and an opposite, distal end adapted for connection to a patient;

an expiratory valve connected to said inspiratory line at a distance from said distal end of said inspiratory line to evacuate gas exhaled by a patient;

at least one measuring instrument selected from the group consisting of a pressure gauge and a flow meter, connected to measure at least one measured characteristic, selected from the group of measured characteristics consisting of pressure and flow rate, of gas in said inspiratory line, said at least one measuring instrument being connected to said inspiratory line between said expiratory valve and said distal end of said inspiratory line; and control means, supplied with said at least one measured characteristic from said at least one measuring instrument, for opening said expiratory valve and simultaneously regulating a flow of said gas from said gas flow generator through said inspiratory line during expiration, dependent on said at least one measured characteristic, for maintaining a positive end-expiratory pressure.

2. A ventilator as claimed in claim 1 wherein said control unit comprises means for detecting, from said at least one measured characteristic, spontaneous efforts of a patient to inhale during expiration, and for closing said expiratory valve and regulating an inspiratory flow of gas whenever a spontaneous attempt at inhalation is detected.

3. A ventilator as claimed in claim 1 wherein said inspiratory line comprises an inspiratory line wall surrounding a gas flow channel, said inspiratory line wall having at least one channel therein, proceeding substantially parallel to said gas flow channel, said at least one channel being connected to said at least one measuring instrument, and said at least one channel having an opening communicating into said gas flow channel between said expiratory valve and said distal end of said inspiratory line.

4. A ventilator as claimed in claim 3 wherein said gas flow channel in said inspiratory line has a constriction therein disposed between the expiratory valve and the distal end of the inspiratory line, wherein said opening of said at least one channel into said gas flow channel is disposed at a side of said constriction facing said distal end, and wherein said inspiratory line further comprises a further channel disposed in said wall of said inspiratory line, proceeding substantially parallel to said gas flow channel, said further channel having an opening communicating into said gas flow channel at a side of said constriction facing said expiratory valve.

5. A ventilator as claimed in claim 1 wherein said expiratory valve comprises a pneumatically controlled ON/OFF valve, connectable to said gas flow generator and to ambient atmosphere via a switching valve, and wherein said control means comprises means for controlling said switching valve for connecting said expiratory valve to said gas flow generator during inspiratory phases and to ambient atmosphere during expiratory phases.

6. A ventilator as claimed in claim 1 wherein said gas flow generator comprises a turbine connected to ambient atmosphere, a pressure tank connected to the turbine, and a control valve connected to the pressure tank in series with the turbine.

7. A ventilator as claimed in claim 1 further comprising at least one dispensing unit and a dispensing channel for dispensing an additive from said dispensing unit to a patient in the gas supplied by said gas flow generator.

8. A ventilator as claimed in claim 7 wherein said inspiratory line comprises an inspiratory line wall surrounding a gas flow channel, and further comprising a dispensing channel disposed in said wall of said inspiratory line, said dispensing channel being connected to said dispensing unit and communicating into said gas flow channel between said expiratory valve and said distal end of said inspiratory line.

9. A ventilator as claimed in claim 1 further comprising gas analysis means for extracting gas specimens for analysis of said gas specimens.

10. A ventilator as claimed in claim 9 wherein said inspiratory line has an inspiratory line wall surrounding a gas flow channel, and further comprising a gas sampling channel disposed in said inspiratory line wall proceeding substantially parallel to said gas flow channel, said gas sampling channel being connected to said gas analysis means and communicating into said gas flow channel between said expiratory valve and said distal end of said inspiratory line.

* * * * *